United States Patent [19]

Rohrmann

[11] Patent Number: 5,391,789
[45] Date of Patent: Feb. 21, 1995

[54] BRIDGED, CHIRAL METALLOCENES, PROCESSES FOR THEIR PREPARATION AND THEIR USE AS CATALYSTS

[75] Inventor: Jürgen Rohrmann, Kelkeim, Germany

[73] Assignee: Hoechst Aktiengesellschaft, Frankfurt am Main, Germany

[21] Appl. No.: 925,985

[22] Filed: Aug. 5, 1992

[30] Foreign Application Priority Data

Aug. 8, 1991 [DE] Germany ............... 4126234

[51] Int. Cl.$^6$ .......................... C07F 17/00; C08F 4/44
[52] U.S. Cl. ......................................... 556/11; 556/1; 556/53; 526/126; 526/127; 526/160
[58] Field of Search ............... 556/53, 11, 1; 526/126, 526/127, 160

[56] References Cited

U.S. PATENT DOCUMENTS 4,769,510 9/1988 Kaminsky et al. .................... 585/512

FOREIGN PATENT DOCUMENTS

| | | |
|---|---|---|
| 0316155 | 5/1989 | European Pat. Off. . |
| 0185918 | 9/1989 | European Pat. Off. . |
| 0351391 | 1/1990 | European Pat. Off. . |
| 0420436 | 4/1991 | European Pat. Off. . |
| 0423101 | 4/1991 | European Pat. Off. . |
| 0426643 | 5/1991 | European Pat. Off. . |
| 3826075 | 2/1990 | Germany . |
| 89/5789 | 4/1990 | South Africa . |

OTHER PUBLICATIONS

Wild, Ferdinand et al., *J. Organomet. Chem.* 288, 63–67 (1985).

*Primary Examiner*—José G. Dees
*Assistant Examiner*—Porfirio Nazairo
*Attorney, Agent, or Firm*—Connolly & Hutz

[57] ABSTRACT

Bridged, chiral metallocenes, processes for their preparation and their use as catalysts Metallocenes of the formula I

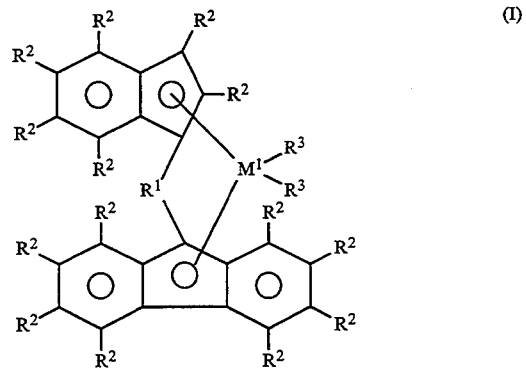

in which, preferably, $M^1$ is titanium, zirconium or hafnium, $R^1$ is a radical

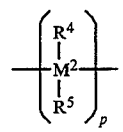

in which $M^2$ is carbon or silicon, $R^4$ and $R^5$ are identical and are hydrogen or an alkyl group, p is 1 or 2, $R^2$ is hydrogen or an alkyl group and the radicals $R^3$ are identical and are halogen or an alkyl group, form, together with an aluminoxane as a cocatalyst, a suitable catalyst system for olefin polymerization.

18 Claims, No Drawings

BRIDGED, CHIRAL METALLOCENES, PROCESSES FOR THEIR PREPARATION AND THEIR USE AS CATALYSTS

The present invention primarily relates to novel bridged, chiral metallocenes which can advantageously be employed as catalyst components in the preparation of high molecular weight polyethylene or of polymers of higher α-olefins having a reduced tacticity.

High molecular weight polyethylene is suitable for the preparation of hollow articles and moldings, while polymers having a reduced tacticity can be used, for example, as a coating material or for the production of roof sheeting.

Bridged metallocenes, in combination with aluminoxanes, are highly active stereospecific catalysts for the preparation of polyolefins (U.S. Pat. No. 4,769,510). The catalytic properties of these systems and the structure of the polymers formed are essentially determined by the structure of the ligand system on the central atom of the metallocene. In addition to electronic and steric factors, the symmetry of the ligand system plays a large role here (New. J. Chem. 102 (1990) 499).

If a chiral metallocenes are employed in the polymerization of a 1-olefin such as propylene, a tactic polypropylene is formed.

If chiral metallocenes having a $C_2$-symmetric ligand system, such as bridged bisindenyl systems or bridged, substituted biscyclopentadienyl systems, are employed in the polymerization of propylene, isotactic polypropylene is formed (EP-A 185 918).

If metallocenes having a $C_3$-symmetric ligand system, such as bridged cyclopentadienyl-fluorenyl systems, are employed in the polymerization of propylene, syndiotactic polypropylene is formed (EP-A 351 391).

If chiral metallocenes having an unsymmetric ligand system, such as bridged cyclopentadienyl-indenyl systems, are employed in the polymerization of propylene, isoblock structures are formed (DE-OS 38 26 075).

There was thus a great interest in employing other structural variants of bridged metallocenes as catalysts for the polymerization of olefins.

Bridged metallocenes in which cyclopentadienyl/cyclopentadienyl, cyclopentadienyl/indenyl, cyclopentadienyl/fluorenyl and indenyl/indenyl combinations are present as π-ligands, and substituted derivatives thereof, are known to date (J. Organomet. Chem. 288 (1985) 63 and EP-A 316 155).

Two structural isomer forms, a racemic and a meso form, are always obtained in the synthesis of indenyl-/indenyl and cyclopentadienyl/cyclopentadienyl complexes. The ratio of the isomers is as a rule 1:1. Preparative separation of these two forms is expensive and in many cases is impossible or only incomplete. The yield of the desired racemic form is moreover therefore greatly reduced.

The pure racemates must be employed as catalysts for the stereospecific polymerization of 1-olefins, since the meso-forms polymerize non-specifically.

The object achieved by the present invention was thus to discover a novel compound class of chiral metallocenes with which expensive removal of the meso-form can be omitted.

The invention thus relates to the compounds of the formula I

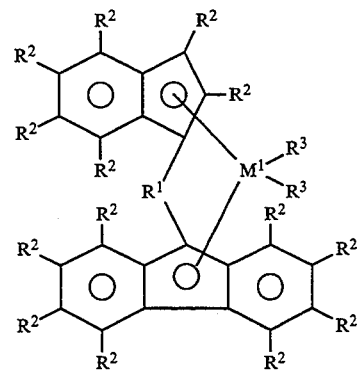

in which $M^1$ is a metal from the group comprising titanium, zirconium, hafnium, vanadium, niobium and tantalum, $R^1$ is

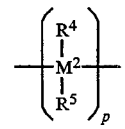

in which $M^2$ is carbon, silicon, germanium or tin, $R^4$ and $R^5$ are identical or different and are a hydrogen atom, a halogen atom, a $C_1$–$C_{10}$-alkyl group, a $C_6$–$C_{10}$-aryl group, a $C_2$–$C_{10}$-alkenyl group, a $C_7$–$C_{40}$-arylalkyl group, a $C_8$–$C_{40}$-arylalkenyl group or a $C_7$–$C_{40}$-alkylaryl group, or $R^4$ and $R^5$, together with the atom joining them, form a ring, and p is 1, 2 or 3, the radicals $R^2$ are identical or different and are hydrogen, a $C_1$–$C_{10}$-alkyl group, a $C_6$–$C_{10}$-aryl group, a $C_2$–$C_{10}$-alkenyl group, a $C_7$–$C_{40}$-arylalkyl group, a $C_8$–$C_{40}$-arylalkenyl group, a $C_7$–$C_{40}$-alkylaryl group or a halogen atom and the radicals $R^3$ are identical or different and are a $C_1$–$C_{10}$-alkyl group, a $C_1$–$C_{10}$-alkoxy group, a $C_6$–$C_{10}$-aryl group, a $C_6$–$C_{10}$-aryloxy group, a $C_2$–$C_{10}$-alkenyl group, a $C_7$–$C_{40}$-arylalkyl group, a $C_8$–$C_{40}$-arylalkenyl group, a $C_7$–$C_{40}$-alkylaryl group, hydrogen or a halogen atom.

In this definition, alkyl is straight chain or branched alkyl and halogen is fluorine, chlorine, bromine or iodine, in particular chlorine.

Preferably, in formula I, $M^1$ is titanium, zirconium or hafnium, $M^2$ is carbon or silicon, $R^4$ and $R^5$ are identical and are hydrogen or a $C_1$–$C_4$-alkyl group, p is 1 or 2, $R^2$ is hydrogen or a $C_1$–$C_4$-alkyl group and the radicals $R^3$ are identical and are halogen or a $C_1$–$C_4$-alkyl group.

In particular, $M^1$ is zirconium, $M^2$ is carbon or silicon, $R^4$ and $R^5$ are identical and are methyl or ethyl, p is 1, $R^2$ is hydrogen or a methyl group and the radicals $R^3$ are identical and are chlorine or methyl.

Preferred representatives of the metallocenes according to the invention which may be mentioned are (isopropylidene(9-fluorenyl)(1-indenyl))zirconium dichloride and (dimethylsilyl(9-fluorenyl)(1-indenyl))zirconium dichloride.

The metallocenes I are chiral and are obtained as the racemate during synthesis. For symmetry reasons, no undesirable meso-form can be formed. The racemate is preferably employed as the catalyst component in the olefin polymerization. The pure R- or S-form can also be used as a polymerization catalyst.

The separation of the stereoisomers is known in principle.

The present invention futhermore relates to a process for the preparation of the metallocenes I, which comprises a) reacting a compound of the formula II

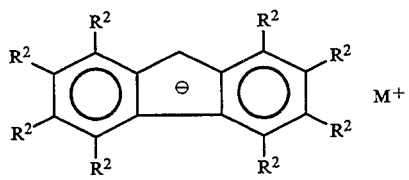
(II)

with a compound of the formula III

X—R¹—X (III)

to give a compound of the formula IV

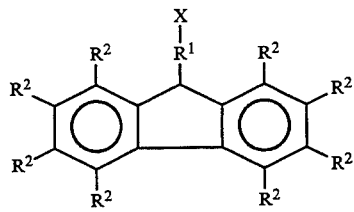
(IV)

and reacting this with a compound of the formula V

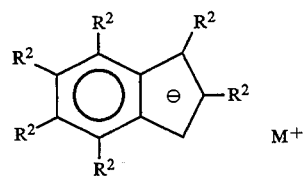
(V)

to give a compound of the formula VI

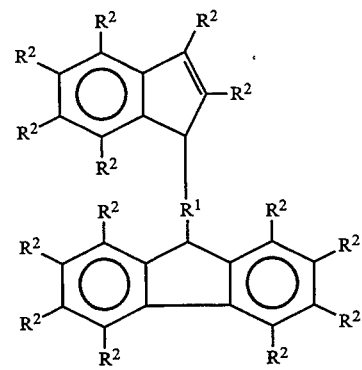
(VI)

in which R¹ and R² have the meanings given for formula I, X is a nucleophilic leaving group, such as halogen or O-tosyl, and M is an alkali metal, or b) for compounds of the formula I where

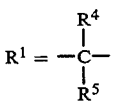

reacting a compound of the formula VII

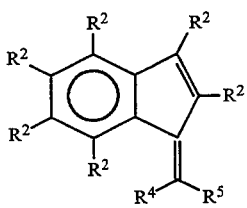
(VII)

with a compound of the formula II to give a compound of the formula VI, in which the substituents have the meanings given for formula I, and reacting the reaction product VI obtained under a) or b) with a compound of the formula VIII

M¹X'₄ (VIII)

in which X' is halogen and M¹ has the meaning given in formula I, and if appropriate forming derivatives of the reaction product thus obtained.

The ligand systems of the formula VI can be reacted by known methods (J. Organomet. Chem. 288 (1985) 63) to give the metallocene dichlorides and with alkylating agents, such as, for example, lithium-alkyls, by methods which are known from the literature (J. Amer. Chem. Soc. 95 (1973) 6263) to give the metallocenes of the general formula (I):

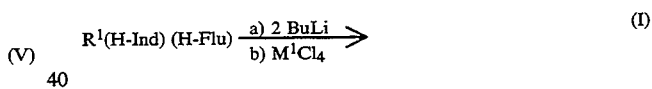

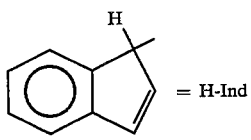

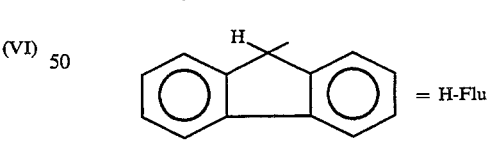

Process variant a):

The fluorenyl anion II (for the preparation, see variant b)), which can also be substituted, is reacted with an excess of reagent of the formula X—R¹—X in an inert solvent (see variant b)), preferably to achieve monosubstitution. For this, the reagent X—R¹—X is initially introduced into the reaction vessel and the fluorenyl anion is added slowly, so that an excess of the bridging reagent is constantly present. Halogen atoms are preferably suitable as the leaving groups X. The monosubstitution product IV is then reacted with the indenyl anion V, which can also be substituted, in a molar ratio of 0.5:1 to 1:0.5, preferably 1:1, in an inert solvent (see variant b)). For this reaction, the monosubstitution product or the indenyl component can be initially introduced into the reaction vessel and the other component can be added, but the indenyl component is preferably added slowly to the monosubstitution product. The reaction temperature is in the range from −78° C. to +120° C., preferably in the range from −40° C. to +40° C.

The indenyl anion is prepared by deprotonation of the corresponding indene or substituted indene (for the preparation, see variant b)) with a strong base in the abovementioned solvents. Suitable agents are butyllithium, sodium hydride, potassium hydride, sodium amide or elemental sodium or potassium.

After the reaction mixture has been worked up by hydrolysis, the ligand systems of the formula VI can be isolated and purified by extraction, recrystallization or column chromatography.

Process variant b) for compounds I where

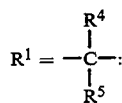

The substituted indenes used as starting substances in accordance with the equation which follows are commercially obtainable or can be prepared by condensation of the five-membered ring onto a substituted aromatic by methods which are known from the literature (Bull. Soc. Chim. Ft., 11 (1973) 3092; Bull. Soc. Chim. Fr., 3 (1967) 987; and J. Org. Chem. 55 (1990) 247).

These indenes are converted into substituted benzofulvenes VII by reaction with ketones of the formula shown below and bases, such as sodium ethanolate in ethanol, by methods which are known from the literature (Annalen, 347 (1906) 257). These products are then reacted with the anion of fluorene, which can also be substituted, in a molar ratio of 0.5:1 to 1:0.5, preferably 1:1, in an inert solvent. Suitable solvents are aliphatic or aromatic hydrocarbons or ethers. Tetrahydrofuran, diethyl ether and toluene are particularly suitable. The benzofulvene or the fluorenyl component II can be initially introduced into the reaction vessel and the other component can be added, but the benzofulvene is preferably added dropwise to the fluorenyl component. The reaction temperature is in the range from −78° C. to +120° C., preferably in the range from −40° C. to +40° C. The reaction time is 1 to 100 hours, preferably 8 to 24 hours.

The fluorenyl anion is prepared by deprotonation of the commercially obtainable fluorene derivatives with a strong base in the abovementioned solvents. Butyllithium, sodium hydride, potassium hydride, sodium amide or elemental sodium or potassium are suitable.

After the reaction mixture has been worked up by hydrolysis, the ligand systems of the formula VI can be isolated and purified by extraction, recrystallization or column chromatography.

The ligand systems of the formula VI can thus be prepared in principle in accordance with the following equations Variant b)

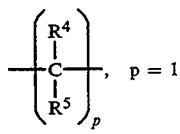

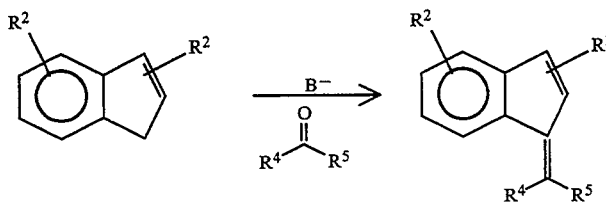 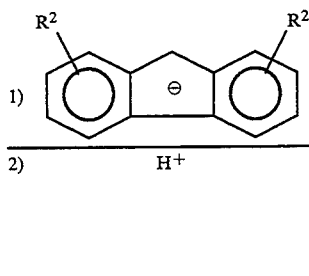

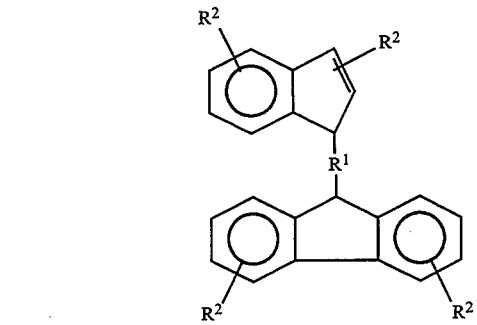

Variant a)

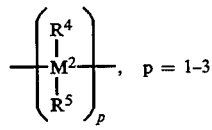

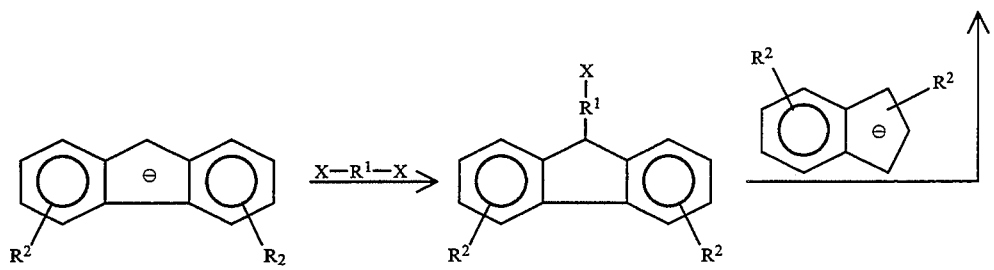

(X = Cl, Br, I, O-tosyl or similar leaving groups)

The metallocenes of the formula I are suitable catalyst components for olefin polymerization.

The present invention thus also relates to the use of the metallocenes I as a catalyst component in olefin polymerization.

A cocatalyst which is preferably used in the olefin polymerization is an aluminoxane of the formula (A)

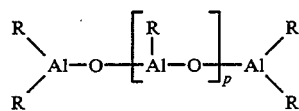
(A)

for the linear type, and/or of the formula (B)

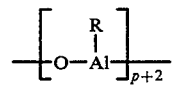
(B)

for the cyclic type, in which, in the formulae (A) and (B), the radicals R can be identical or different and are a $C_1$-$C_6$-alkyl group, a $C_6$-$C_{18}$-aryl group or hydrogen and p is an integer from 2 to 50, preferably 10 to 35.

Preferably, the radicals R are identical and are methyl, isobutyl, phenyl or benzyl, particularly preferably methyl.

If the radicals R are different, they are preferably methyl and hydrogen, or alternatively methyl and isobutyl, hydrogen or isobutyl preferably being contained in the radicals to the extent of 0.01–40% (number of radicals R).

The aluminoxane can be prepared in various ways by known processes. One of the methods is, for example, to react an aluminum-hydrocarbon compound and/or a hydridoaluminum-hydrocarbon compound with water (gaseous, solid, liquid or bonded—for example as water of crystallization) in an inert solvent (such as, for example, toluene). To prepare an aluminoxane having different alkyl groups R, two different aluminum-trialkyls ($AlR_3 + AlR'_3$) are reacted with water according to the desired composition (compare S. Pasynkiewicz, Polyhedron 9 (1990) 429 and EP-A 302 424).

The precise structure of the aluminoxanes A and B is unknown.

Regardless of the type of preparation, all aluminoxane solutions have the common feature of a varying content of unreacted aluminum starting compound, which is present in the free form or as an adduct.

It is possible for the metallocene I to be preactivated with an aluminoxane of the formula A and/or B before use in the polymerization reaction. This significantly increases the polymerization activity and improves the particle morphology.

The preactivation of the transition metal compound is carried out in solution. For this operation, the metallocene is preferably dissolved in a solution of the aluminoxane in an inert hydrocarbon. An aliphatic or aromatic hydrocarbon is a suitable inert hydrocarbon. Toluene is preferably used.

The concentration of the aluminoxane in the solution is in the range from about 1% by weight up to the saturation limit, preferably from 5 to 30% by weight, in each case based on the total solution. The metallocene can be employed in the same concentration, but is preferably employed in an amount of $10^{-4}$–1 mol per mol of aluminoxane. The preactivation time is 5 minutes to 60 hours, preferably 5 to 60 minutes. The operation is carried out at a temperature of $-78°$ C. to $100°$ C., preferably $0°$ to $70°$ C.

The metallocene can also be prepolymerized or applied to a support. The (or one of the) olefin(s) employed in the polymerization is (are) preferably used for the prepolymerization.

Suitable supports are, for example, silica gels, aluminum oxides, solid aluminoxane or other inorganic support materials. A polyolefin powder in finely divided form is also a suitable support material.

Another possible embodiment of the process comprises using a salt-like compound of the formula $R_xNH_{4-x}BR'_4$ or of the formula $R_3PHBR'_4$ as the cocatalyst, instead of or in addition to an aluminoxane. In this formula, x is 1, 2 or 3, R is identical or different alkyl or aryl and R' is aryl, which can also be fluorinated or partly fluorinated. In this case, the catalyst consists of the reaction product of a metallocene with one of the compounds mentioned (cf. EP-A 277 004).

The polymerization or copolymerization is carried out in a known manner in solution, in suspension or in the gas phase, continuously or discontinuously in one or more stages, at a temperature of $0°$ to $150°$ C., preferably $30°$ to $80°$ C. Olefins of the formula $R^a$—CH=CH—$R^b$ are polymerized or copolymerized. In this formula, $R^a$ and $R^b$ are identical or different and are a hydrogen atom or an alkyl radical having 1 to 14 carbon atoms.

Propylene and ethylene are polymerized in particular.

Hydrogen is added as a molecular weight regulator, if necessary. The overall pressure in the polymerization system is 0.5 to 100 bar. Polymerization in the pressure range of 5 to 64 bar, which is of particular industrial interest, is preferred.

The metallocene is used in this reaction in a concentration, based on the transition metal, of $10^{-3}$ to $10^{-8}$, preferably $10^{-4}$ to $10^{-7}$ mol of transition metal per dm$^3$ of solvent or per dm$^3$ of reactor volume. The aluminoxane is used in a concentration of $10^{-5}$ to $10^{-1}$ mol, preferably $10^{-4}$ to $10^{-2}$ mol, per dm$^3$ of solvent or per dm$^3$ of reactor volume. In principle, however, higher concentrations are also possible.

If the polymerization is carried out as suspension or solution polymerization, an inert solvent which is customary for the Ziegler low-pressure process is used. For example, the polymerization is Carried out in an aliphatic or cycloaliphatic hydrocarbon; examples of these which may be mentioned are butane, pentane, hexane, heptane, isooctane, cyclohexane and methylcyclohexane. A gasoline or hydrogenated diesel oil fraction can furthermore be used. Toluene is also suitable. The polymerization is preferably carried out in the liquid monomer.

If inert solvents are used, the monomers are metered in as a gas or in liquid form.

The polymerization can be carried out for any desired period of time, since the catalyst system to be used according to the invention shows only a slight time-dependent drop in polymerization activity.

The following examples are intended to illustrate the invention in more detail.

All the following working operations were carried out under an Ar atmosphere (Schlenk technique), unless stated otherwise.

EXAMPLE 1

Isopropylidene(9-fluorenyl)-1-indene (1)

24.1 ml (60.2 mmol) of a 2.5M butyllithium solution in hexane were added to a solution of 10.2 g (60.2 mmol) of fluorene in 65 ml of tetrahydrofuran at room temperature. The mixture was then heated under reflux for a further hour. 9.9 g (60.2 mmol) of benzofulvene (for the preparation, see Annalen 347 (1906) 257) were dissolved in 50 ml of tetrahydrofuran, and the solution was added dropwise to the red solution of the lithium-fluorene at room temperature in the course of 4 hours. The solution was then stirred at room temperature for 16 hours and heated under reflux for a further 2 hours. The dark brown reaction mixture was poured onto ice and extracted with methylene chloride. The combined organic phases were dried over sodium sulfate and concentrated to dryness. The residue was chromatographed on 550 g of silica gel 60 using a mobile phase mixture of hexane/methylene chloride, the proportion of methylene chloride being increased gradually from 3% to 8% in the course of the chromatography.

About 6 g of a mixture of fluorene and benzofulvene were to be eluted first. 2.8 g (14%) of the compound 1 were then eluted (colorless solid). Yield 14% (18%, based on the educt reacted).

$^1$H-NMR spectrum (CDCl$_3$): 7.0-8.1 (12,m,arom.-H), 6.05 (1,t,ind-H), 4.75 (1,s,flu-H), 3.42 (2,d,ind-H2), 1.20 (6,s,CH$_3$).

EXAMPLE 2

Isopropylidene(9-fluorenyl)-1-indene (1)

Analogous to Example 1. However, the benzofulvene solution was added dropwise to the lithium-fluorene solution at the boiling point in the course of 4 hours. The mixture was then stirred at room temperature for 17 hours and heated under reflux for a further 4 hours. Working up was as in Example 1. Column chromatography gave 3.2 g of the compound 1 (colorless crystalline powder). Yield 17% (22%, based on the educt reacted).

EXAMPLE 3

Isopropylidene(9-fluorenyl)-1-indene (1)

Analogous to Example 1. However, the benzofulvene solution was added dropwise to the lithium-fluorene solution at $-78°$ C. in the course of 20 minutes. The mixture was warmed to room temperature in the course of 17 hours and stirred at room temperature for i hour. Working up was as in Example 1. Column chromatography gave 9.8 g of the compound 1 in the form of a white crystalline powder. The yield was 51%.

EXAMPLE 4

[Isopropylidene(9-fluorenyl)(1-indenyl)]zirconium dichloride (2)

3.2 g (9.9 mmol) of the ligand system 1 were suspended in 45 ml of diethyl ether, and 8.7 ml (21.8 mmol) of a 2.5M butyllithium solution in hexane were added at room temperature, during which the suspension initially dissolved and assumed a pale yellow color. After the mixture had been stirred at room temperature for 21 hours, 8 ml of hexane were added to the orange suspension formed. The orange-colored precipitate was filtered off with suction over a G3 frit, washed with hexane and dried at 50° C. under an oil pump vacuum for 6 hours. The pale red powder was suspended in 30 ml of toluene, and 2.3 g (9.9 mmol) of ZrCl$_4$ were added at 0° C. After the mixture had been stirred at room temperature for 30 minutes, the precipitate formed was filtered off, washed with 10 ml of toluene and dried in an oil pump vacuum.

4.4 g of the complex 2 were obtained as a red-violet powder. Crude yield 92%. For further purification of the compound, the residue was stirred with a small amount of tetrahydrofuran at $-30°$ C. in order to dissolve impurities. Pure yield 30%. Mass spectrum (direct vaporization, EI (70 eV), CI (isobutane)): 480 M$^+$ (correct dissociation).

$^1$H-NMR spectrum (CDCl$_3$): 6.7–8.1 (12, arom.-H), 6.50 (1,dd,$\beta$-ind-H), 6.07 (1,d,$\alpha$-ind-H), 2.92 (3,s,CH$_3$), 2.60 (3,s,CH$_3$).

EXAMPLE 5

[Isopropylidene(9-fluorenyl)(1-indenyl)]zirconium dichloride (2)

3.0 g (9.3 mmol) of the ligand system 1 were reacted with butyllithiumin diethyl ether and the mixture was worked up, analogously to Example 1. However, the dilithium salt was added to a suspension of 2.0 g (8.4 mmol) of ZrCl$_4$ in 40 ml of toluene at $-78°$ C. The mixture was heated to 0° C. in the course of 80 minutes and stirred at 0° C. for a further 30 minutes. The red-violet precipitate was filtered off, dried in an oil pump vacuum and stirred with 10 ml of tetrahydrofuran at $-40°$ C. to dissolve impurities. The red-violet suspension was filtered over a G3 frit. After drying in an oil pump vacuum, 1.6 g of the complex 2 were obtained as a red-violet powder. Pure yield 40% (correct $^1$H-NMR spectrum and mass spectrum).

EXAMPLE 6

Dimethylsilyl(9-fluorenyl)-1-indene (3)

24 ml (60.2 mmol) of a 2.5M butyllithium solution in hexane were added to a solution of 10 g (60.2 mmol) of fluorene in 100 ml of tetrahydrofuran at room temperature and the mixture was heated under reflux for a further 30 minutes. The red solution was slowly added dropwise, at room temperature, to 23.2 g (180 mmol) of dimethyldichlorosilane dissolved in 150 ml of tetrahydrofuran. After the mixture had been stirred at room temperature for 16 hours, the solvent was stripped off and the yellowish oil which remained was freed from excess dimethyldichlorosilane in an oil pump vacuum. The yellowish solid was dissolved in 100 ml of tetrahydrofuran, and 60.2 mmol of lithiumindenyl, prepared from 7.6 g (60.2 mmol) of indene and 60 mmol of butyllithium in 100 ml of tetrahydrofuran, were slowly added at room temperature. After the mixture had been stirred at room temperature for 16 hours, it was poured onto ice, rendered neutral and extracted with diethyl ether. The residue which remained after the solvent had been stripped off was chromatographed over silica gel 60. A mixture of indene and fluorene was first eluted with a mobile phase mixture of hexane/ethyl acetate (10:1). Thereafter, the product 3 followed, and then the compound dimethylsilylbis(9-fluorene). For further purification, the mixed fraction was chromatographed again using a mobile phase mixture of hexane/diethyl ether (40:1). A total of 1.9 g of the pure compound 3 were obtained as a white powder. Yield 10%. $^1$H-NMR spectrum (CDCl$_3$): 2 double bond isomers (A:B=2:1), 7.0–7.9 (arom.-H), 6.82 (m,ind-H,A), 6.60 (t,ind-H,B), 6.32 (dd,ind-H,A), 4.17 (s,flu-H,B), 4.05 (s,flu-H,A), 3.57 (t,ind-H,A), 3.40 (d,ind-H,B), several signals of the SiCH$_3$ groups in the region from 0 to −1 ppm.

EXAMPLE 7

[Dimethylsilyl(9-fluorenyl)(1-indenyl)]zirconium dichloride (4)

1.84 g (5.44 mol) of the ligand system 3 were dissolved in 20 ml of diethyl ether, and 5.44 ml (13.6 mmol) of a 2.5M butyllithium solution in hexane were slowly added at room temperature. After the mixture had been stirred at room temperature for 4 hours, hexane was added to the orange-yellow suspension and the suspension was filtered over a G3 frit. The orange-yellow powder was washed with 10 ml of hexane and dried in an oil pump vacuum for a long time. 1.16 g (5.0 mmol) of ZrCl$_4$ were suspended in 20 ml of CH$_2$Cl$_2$, and the dilithium salt was added at −78° C. The mixture was warmed to room temperature in the course of 2 hours and filtered over a G3 frit. The solid was washed again with 5 ml of CH$_2$Cl$_2$ and dried in an oil pump vacuum. 1.2 g of the complex 4 were obtained as pink-colored powder. Crude yield 46%. For complete purification of the complex, the crude product was stirred in a small amount of tetrahydrofuran at 0° C., impurities dissolving. Pure yield 25%. Mass spectrum (direct vaporization, EI (80 eV)): 496 M+ (correct dissociation, correct isotope pattern). $^1$H-NMR spectrum (CDCl$_3$): 6.9–8.1 (m,12,arom.-H), 6.77 (dd, 1,β-ind-H), 5.95 (d,1,α-ind-H), 1.55 (s,3,CH$_3$), 1.27 (s,3,CH$_3$).

EXAMPLE 8

[Dimethylsilyl(9-fluorenyl)(1-indenyl)]hafnium dichloride (5)

1.50 g (4.43 mmol) of the ligand system 3 were dissolved in 20 ml of diethyl ether and, analogously to Example 7, was reacted with butyllithium and the mixture was worked up. The dillithium salt was then reacted with 1.42 g (4.43 mmol) of HfCl$_4$ in methylene chloride at −78° C. and the mixture was worked up, analogously to Example 7. 1.09 g of the complex 5 were obtained in the form of a reddish powder as the crude product. Crude yield 42%. For purification, the powder was stirred with a small amount of THF at −10° C. Pure yield 20%. Mass spectrum (direct vaporization, EI (80 eV)): 587 M+ (based on $^{180}$Hf, correct dissociation, correct isotope pattern). $^1$H-NMR spectrum (CDCl$_3$): 7.0–8.1 (m, 12,arom.-H), 6.61 (dd, 1,β-ind-H), 5.89 (d,1,α-ind-H), 1.53 (s,3,CH$_3$), 1.25 (s,3,CH$_3$).

POLYMERIZATION EXAMPLES

Example A

A dry 16 dm$^3$ reactor was flushed with nitrogen and 10 dm$^3$ of a dearomatized gasoline cut having a boiling range of 100° to 120° C. were introduced at 20° C.

The gas space of the boiler was then flushed free from nitrogen by forcing in 2 bar of ethylene and letting down, 5 times in each case.

30 cm$^3$ of a toluene solution of methylaluminoxane (corresponding to 45 mmol of Al, molecular weight according to cryoscopic determination 750 g/mol) were then added.

The contents of the reactor were heated up to 60° C. in the course of 15 minutes, while stirring, and the overall pressure was adjusted to 5 bar at a stirring speed of 250 revolutions per minute by addition of ethylene.

In parallel with this, 1.3 mg of dimethylsilyl(9-fluorenyl)(1-indenyl)zirconium dichloride were dissolved in 20 cm$^3$ of a toluene solution of methylaluminoxane and were preactivated by leaving the mixture to stand for 15 minutes. The solution was then introduced into the reactor and the polymerization system was brought to a temperature of 70° C. and kept at this temperature for 1 hour by appropriate cooling. The overall pressure during this time was kept at 5 bar by appropriate introduction of ethylene.

140 g of polyethylene were obtained. The viscosity number was 380 cm$^3$/g.

Example B

A dry 16 dm$^3$ reactor was flushed with nitrogen, and 10 dm$^3$ of liquid propylene were introduced.

30 cm$^3$ of a toluene solution of methylaluminoxane (corresponding to 45 mmol of Al, average degree of oligomerization n=16) were then added and the mixture was stirred at 30° C. for 15 minutes.

In parallel with this, 30.4 mg of isopropylidene (9-fluorenyl)(1-indenyl) zirconium dichloride were dissolved in 20 cm$^3$ of a toluene solution of methylaluminoxane (30 mmol of Al) and were preactivated by leaving the mixture to stand for 15 minutes.

The solution was then introduced into the reaction, the mixture was heated up to the polymerization temperature of 70° C. (4° C./min) by supplying heat and the polymerization system was kept at 70° C. for 1 hour by cooling. The polymerization was stopped by addition of 20 ml of isopropanol. The excess monomer was removed as waste gas. 170 g of a highly viscous, tacky oil were obtained.

I claim:

1. A compound of the formula I

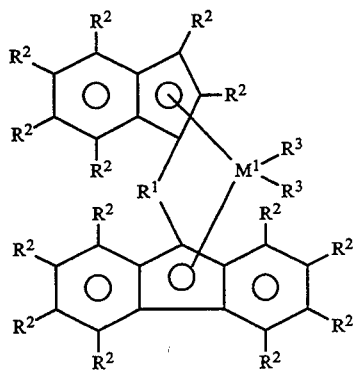

(I)

in which M¹ is a metal from the group comprising titanium, zirconium, hafnium, vanadium, niobium and tantalum, R¹ is

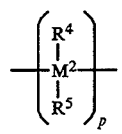

in which M² is carbon, silicon, germanium or tin, R⁴ and R⁵ are identical or different and are a hydrogen atom, a halogen atom, a $C_1$–$C_{10}$-alkyl group, a $C_6$–$C_{10}$-aryl group, a $C_2$–$C_{10}$-alkenyl group, a $C_7$–$C_{40}$-arylalkyl group, a $C_8$–$C_{40}$-arylalkenyl group or a $C_7$–$C_{40}$-alkylaryl group, or R⁴ and R⁵, together with the atom joining them, form a ring, and p is 1, 2 or 3, the radicals R² are identical or different and are hydrogen, a $C_1$–$C_{10}$-alkyl group, a $C_6$–$C_{10}$-aryl group, a $C_2$–$C_{10}$-alkenyl group, a $C_7$–$C_{40}$-arylalkyl group, a $C_8$–$C_{40}$-arylalkenyl group, a $C_7$–$C_{40}$-alkylaryl group or a halogen atom and the radicals R³ are identical or different and are a $C_1$–$C_{10}$-alkyl group, a $C_1$–$C_{10}$-alkoxy group, a $C_6$–$C_{10}$-aryl group, a $C_6$–$C_{10}$-aryloxy group, a $C_2$–$C_{10}$-alkenyl group, a $C_7$–$C_{40}$-arylalkyl group, a $C_8$–$C_{40}$-arylalkenyl group, a $C_7$–$C_{40}$-alkylaryl group, hydrogen or a halogen atom.

2. A compound of the formula I as claimed in claim 1, in which, in formula I, M¹ is titanium, zirconium or hafnium, M² is carbon or silicon, R⁴ and R⁵ are identical and are hydrogen or a $C_1$–$C_4$-alkyl group, p is 1 or 2, R² is hydrogen or a $C_1$–$C_4$-alkyl group and the radicals R³ are identical and are halogen or a $C_1$–$C_4$-alkyl group.

3. A compound of the formula I as claimed in claim 1, in which, in formula I, M¹ is zirconium, M² is carbon or silicon, R⁴ and R⁵ are identical and are methyl or ethyl, p is 1, R² is hydrogen or a methyl group and the radicals R³ are identical and are chlorine or methyl.

4. Isopropylidene(9-fluorenyl)(1-indenyl)zirconium dichloride or dimethylsilyl(9-fluorenyl)(1-indenyl)zirconium dichloride.

5. A process for the preparation of a compound of the formula I as claimed in claim 1, which comprises
a) reacting a compound of the formula II

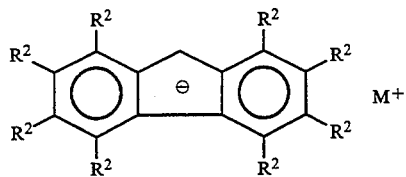

(II)

with a compound of the formula III

X—R¹—X   (III)

to give a compound of the formula IV

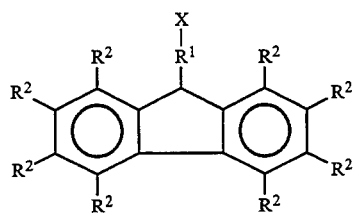

(IV)

and reacting this with a compound of the formula V

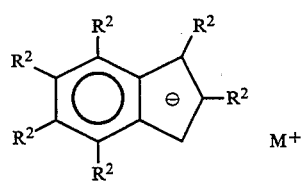

(V)

to give a compound of the formula VI

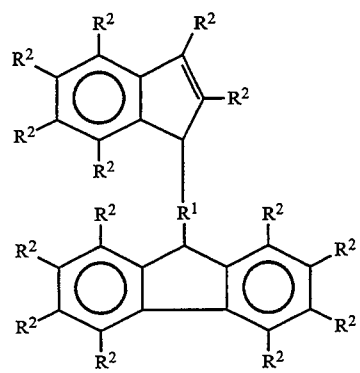

(VI)

in which R¹ and R² have the meanings given for formula I, X is a nucleophilic leaving group, and M is an alkali metal, or b) for a compound of the formula I where

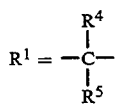

reacting a compound of the formula VII

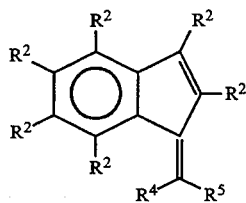

with a compound of the formula II to give a compound of the formula VI, in which the substituents have the meanings given for formula I, and reacting the reaction product VI obtained under a) or b) with a compound of the formula VIII $$M^1X'_4 \qquad (VIII)$$

in which X' is halogen and $M^1$ has the meaning given in formula I, and optionally forming derivatives of the reaction product thus obtained by reaction with alkylating agents.

6. A method for polymerizing an olefin to obtain a polyolefin, comprising the step of:
carrying out the polymerization in solution, in suspension or in the gas phase, at a temperature of 0° to 150° C., and at a pressure of 0.5 to 100 bar, presence of a catalyst comprising a compound of formula I

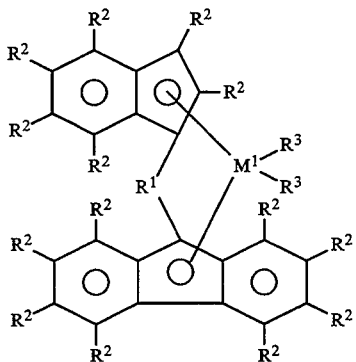

in which $M^1$ is a metal selected from the group consisting of titanium, zirconium, hafnium, vanadium, niobium and tantalum,
$R^1$ is

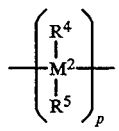

in which $M^2$ is carbon, silicon, germanium or tin, $R^4$ and $R^5$ are identical or different and are a hydrogen atom, a halogen atom, a $C_1$–$C_{10}$-alkyl group, a $C_6$–$C_{10}$-aryl group, a $C_2$–$C_{10}$-alkenyl group, a $C_7$–$C_{40}$-arylalkyl group, a $C_8$–$C_{40}$-arylalkenyl group or a $C_7$–$C_{40}$-alkylaryl group, or $R^4$ and $R^5$, together with the atom joining the, form a ring, and p is 1.2 or 3, the radicals $R^2$ are identical or different and are hydrogen, a $C_1$–$C_{10}$-alkyl group, a $C_6$–$C_{10}$-aryl group, a $C_2$–$C_{10}$-alkenyl group, a $C_7$–$C_{40}$-arylalkyl group, a $C_8$–$C_{40}$-arylalkenyl group a $C_7$–$C_{40}$-alkylaryl group or a halogen atom and the radicals $R^3$ are identical or different and are a $C_1$–$C_{10}$-alkyl group, a $C_1$–$C_{10}$-alkoxy group, a $C_6$–$C_{10}$-aryl group, a $C_6$–$C_{10}$-aryloxy group, a $C_2$–$C_{10}$-alkenyl group, a $C_7$–$C_{40}$-arylalkyl group, a $C_8$–$C_{40}$-arylalkenyl group, a $C_7$–$C_{40}$-alkylaryl group, hydrogen or a halogen atom.

7. Compound as claimed in claim 1, wherein $R^4$ and $R^5$ are identical or different and are methyl, ethyl, hydrogen or chlorine.

8. The process as claimed in claim 5, wherein X is a halogen or O-tosyl.

9. The method as claimed in claim 6, further comprising a co-catalyst which is an aluminoxane of the formula (A)

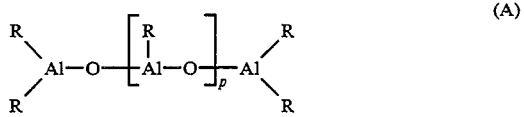

for the linear type, and/or of the formula (B)

for the cyclic type, in which, in the formulae (A) and (B), the radicals R can be identical or different and are a $C_1$–$C_6$-alkyl group, a $C_6$–$C_{18}$-aryl group or hydrogen and p is an integer from 2 to 50.

10. The method as claimed in claim 9, wherein p is an integer from 10 to 35.

11. The method as claimed in claim 9, wherein R is identical and is methyl, isobutyl, phenyl or benzyl.

12. The method as claimed in claim 10, wherein R is identical and is methyl.

13. The method as claimed in claim 9, wherein R is different and is methyl and hydrogen.

14. The method as claimed in claim 9, wherein R is different and is methyl and isobutyl and hydrogen.

15. The method as claimed in claim 14, wherein the isobutyl being contained in the radicals is to the extent of 0.1–40% (number of radicals R).

16. The process as claimed in claim 6, wherein said temperature is from 30° to 80° C. and said pressure is from 5 to 64 bar.

17. The method as claimed in claim 6, wherein said olefin is of the formula $R^aCH{=}CH{-}R^b$ wherein $R^a$ and $R^b$ are identical or different and are a hydrogen atom or an alkyl radical having 1 to 14 carbons.

18. The method as claimed in claim 17, wherein said olefin is propylene or ethylene.

* * * * *

Adverse Decisions In Interference

Patent No. 5,391,789, Jurgen Bohrmann, BRIDGES, CHIRAL METALLOCENES, PROCESSES FOR THEIR PREPARATION AND THEIR USE AS CATALYSTS, Interference No. 104,626, final judgment adverse to the patentee rendered June 27, 2001, as to claims 6, 9-18.
*(Official Gazette July 31, 2001)*